US012746103B2

(12) United States Patent
Tavor

(10) Patent No.: US 12,746,103 B2
(45) Date of Patent: Sep. 29, 2026

(54) MULTI-DIRECTIONAL DENTAL SUCTION-MIRROR TOOL

(71) Applicant: RNDENT-IP LTD., Hod Hasharon (IL)

(72) Inventor: David Tavor, Hod Hasharon (IL)

(73) Assignee: RNDENT-IP LTD., Hod Hasharon (IL)

( * ) Notice: Subject to any disclaimer, the term of this patent is extended or adjusted under 35 U.S.C. 154(b) by 46 days.

(21) Appl. No.: 18/852,761

(22) PCT Filed: Mar. 28, 2023

(86) PCT No.: PCT/IL2023/050320
§ 371 (c)(1),
(2) Date: Sep. 30, 2024

(87) PCT Pub. No.: WO2023/194986
PCT Pub. Date: Oct. 12, 2023

(65) Prior Publication Data

US 2025/0248796 A1 Aug. 7, 2025

(30) Foreign Application Priority Data

Apr. 7, 2022 (IL) ........................................ 292058

(51) Int. Cl.

| | |
|---|---|
| ***A61C 17/06*** | (2006.01) |
| ***A61B 1/00*** | (2006.01) |
| ***A61B 1/253*** | (2006.01) |

(52) U.S. Cl.
CPC .......... *A61C 17/088* (2019.05); *A61B 1/0011* (2013.01); *A61B 1/253* (2013.01)

(58) Field of Classification Search
CPC .. A61C 7/06; A61C 7/08; A61C 7/088; A61B 1/0011; A61B 1/24; A61B 1/247;
(Continued)

(56) References Cited

U.S. PATENT DOCUMENTS

| | | | | |
|---|---|---|---|---|
| 1,821,137 A * | 9/1931 | Bostock | A45D 42/08 | 52/393 |
| 3,014,279 A * | 12/1961 | Fosdal | A61B 1/253 | 359/882 |
| 3,102,338 A * | 9/1963 | Warriner | A61C 17/088 | 433/31 |

(Continued)

FOREIGN PATENT DOCUMENTS

| | | |
|---|---|---|
| CN | 2019-58855 U | 9/2011 |
| DE | 1956983 A1 * | 11/1969 |

(Continued)

OTHER PUBLICATIONS

Practicon et al. (https://www.youtube.com/watch?v=voiIVQTTHac, uploaded Jun. 8, 2021). (Year: 2021).*

(Continued)

*Primary Examiner* — Edelmira Bosques
*Assistant Examiner* — Matthew P Saunders
(74) *Attorney, Agent, or Firm* — Ohlandt, Greeley and Perle, L.L.P.

(57) ABSTRACT

A disposable apparatus including: (a) a mirror holder including a floor with a raised circumferential edge having a height≥(Height of a support base+thickness of the mirror); (b) three or more deformable posts distributed around an inner side of said circumferential edge; (c) a plurality of said support bases, each of said bases adjacent to one of said posts on an inner side of the post; and (d) a suction tube with a mouth spanning a plane of a mirror positioned on said bases and a rear opening across said tube from said mouth. Related apparatus and methods are also disclosed.

16 Claims, 5 Drawing Sheets

(58) Field of Classification Search
CPC .... A61B 1/253; G02B 27/0006; G02B 7/182; G02B 5/08
See application file for complete search history.

(56) References Cited

U.S. PATENT DOCUMENTS

| | | | | | |
|---|---|---|---|---|---|
| 3,151,395 | A * | 10/1964 | Moniot | A61B 1/253 433/30 |
| 3,928,916 | A * | 12/1975 | Hansson | A61C 17/088 433/91 |
| 4,512,635 | A * | 4/1985 | Melde | G02B 7/182 433/30 |
| 5,295,826 | A * | 3/1994 | Yandell | A61C 17/08 433/30 |
| 8,133,052 | B1 * | 3/2012 | Emmons, III | A61B 1/00101 433/30 |
| 2018/0263483 | A1 * | 9/2018 | Elazar | A61B 1/247 |
| 2019/0298163 | A1 * | 10/2019 | Tavor | A61B 1/253 |
| 2020/0030068 | A1 * | 1/2020 | Clasen | A61C 17/12 |
| 2023/0122799 | A1 * | 4/2023 | Al Safer | A61B 1/253 433/30 |

FOREIGN PATENT DOCUMENTS

| | | | | |
|---|---|---|---|---|
| EP | 0842634 | A1 * | 5/1998 | A61B 1/247 |
| GB | 2619322 | A * | 12/2023 | A61B 1/247 |
| WO | 2016-207876 | A1 | 12/2016 | |

OTHER PUBLICATIONS

International Search Report dated May 22, 2023 for PCT Application No. PCT/IL2023/050320.
Internet page: (YouTube video) https://www.youtube.com/watch?.

* cited by examiner

SECTION A-A

MULTI-DIRECTIONAL DENTAL SUCTION-MIRROR TOOL

RELATED APPLICATIONS

This application is a national phase application under 35 U.S.C. 371 of PCT/IL2023/050320, filed on Mar. 28, 2023, which claims priority under 35 U.S.C. 119(e) of Israeli application 292058 filed Apr. 7, 2022; each of these earlier applications has the same title and inventor(s) as the present application; and each of these earlier applications is fully incorporated herein by reference thereto.

FIELD OF THE DISCLOSURE

The disclosure is in the field of dentistry tools.

BACKGROUND OF THE DISCLOSURE

Various dental mirrors are used by dentists in order to view inside a patient's mouth. A typical dental mirror consists of a small cylindrical shaft with a metal disk attached at the end of it, which holds the mirror. Typically, such mirrors are biologically inert, environmentally stable and durable, and are capable of being autoclaved and sterilised.

However, the reflective surface of a typical hand-held dental mirror becomes fogged due to moisture and heat in the patient's mouth, or the surface of the mirror becomes non-reflective due to saliva and debris from drilling operations and other dental procedures accumulating on the reflective surface of the mirror.

The conventional method for cleaning debris formed during a dental procedure requires use of a suction tube provided separately from the mirror. In many cases, use of an additional tool requires an additional hand provided by an assistant, since the dentist uses one hand to hold a drill (or surgical instrument) and one hand to hold the mirror. Alternatively or additionally, a cloth is used to periodically remove fog, saliva and debris from the mirror, or the mirror is sprayed with water.

SUMMARY

One aspect of some embodiments of the disclosure relates to a mirror holder formed from thermoplastic polymer and having a raised circumferential edge with three or more deformable posts distributed around an inner side of the raised circumferential edge and a base positioned slightly inward with respect to each of the posts. In some embodiments, the mirror holder includes a suction tube with a mouth facing a mirror positioned in the holder. In some embodiments, dimensions of the mouth are about H2.95 mm/W6.17 mm and the open area of the mouth is about 12.92 $mm^2$. (Measurements are made in a cross-sectional plane of the mouth containing line M-M as depicted in the inset of FIG. 1*d*.)

The suction tube is attachable to a source of suction. In some embodiments, an additional opening is provided in the suction tube opposite the mouth and facing away from the mirror. In some embodiments, dimensions of the additional opening are diameter of about 2.5 mm, and the area of about is 4.96 $mm^2$. (Measurements are made in a cross-sectional plane of the additional opening containing line R-R as depicted in the inset of FIG. 1*d*.) In use, a mirror is laid inside the raised circumferential edge so that it rests on the bases. The posts are then deformed using heat so that they bend over an edge of the mirror and engage and retain it against the bases upon which the mirror is laid. According to various exemplary embodiments of the disclosure three or four or more posts with corresponding bases are deployed around an inner side of the raised circumferential edge. In some exemplary embodiments of the invention, a floor of the mirror holder is provided with raised ribs. In some embodiments, the mirror rests on the ribs, dividing the floor are into discrete airflow zones. Alternatively or additionally, in some embodiments of the disclosure a plurality of slots are provided around the circumferential edge. In some embodiments, each slot facilitates airflow through both the wall (raised circumferential edge) and floor of the mirror holder. In some embodiments, one slot is provided for each discrete airflow zone formed by the mirror resting on the ribs. Alternatively or additionally, in some embodiments when a mirror is engaged and retained by the deformed posts on the bases, there is a space circumferentially surrounding the mirror between an outer edge of the mirror and an inner side of the raised circumferential edge of the holder.

According to another aspect of some embodiments of the invention, the mirror holder includes a floor with a raised circumferential edge extending at least to a plane of a top surface of a mirror seated in the holder. In some embodiments, the mirror holder includes a suction tube with a mouth spanning a plane of a mirror seated in the holder (i.e. the mouth opening extends both above and below the plane of the mirror). In some embodiments, an additional opening (exemplary sizes given above) is provided in the suction tube opposite the mouth and facing away from the mirror. Alternatively or additionally, in some embodiments the mirror holder includes raised ribs on the floor, which function as described above. Alternatively or additionally, in some embodiments of the disclosure a plurality of slots is provided around the circumferential edge. The slots and their function are as described above in the context of the preceding aspect. Alternatively or additionally, in some embodiments the floor of the mirror holder includes a bump at or near its center.

According to still another aspect of some embodiments of the invention, a mirror holder with an integrated suction tube includes an angled collar on the suction tube. In some embodiments, the angled collar matches an end of an extension tube cut at a complementary angle. According to these embodiments, contact of the angled collar with the end of the extension tube cut at a complementary angle contributes to a decrease in relative rotation of the suction tube and the extension tube with respect to one another. Alternatively or additionally, in some embodiments an outer diameter of the suction tube is greater at the collar than an outer diameter of the suction tube at its distal end.

According to a further additional aspect of some embodiments of the invention, a mirror holder with an integrated suction tube which tapers towards an end distal to a portion of the holder that can engage a mirror. According to these embodiments, an extension tube is provided with an end having an inner diameter greater than an outer diameter of the distal end of the suction tube.

According to yet another aspect of some embodiments of the invention, a manufacturing method employs a heated piston to deform three or more deformable posts distributed around a circumferential edge of the holder of a mirror holder tool. According to these embodiments, a mirror positioned on support bases adjacent to each of the posts is engaged and retained on the bases by the deformed posts.

It will be appreciated that the various aspects described above relate to solution of technical problems associated with maintaining a clear image in a mirror during a dental procedure. According to various exemplary embodiments of the disclosure maintaining a clear image includes preventing accumulation of fog and/or debris on a reflective surface of the mirror.

Alternatively or additionally, it will be appreciated that the various aspects described above relate to solution of technical problems related to reducing a frequency with which a dental mirror must be removed from a patient's mouth for cleaning.

Alternatively or additionally, it will be appreciated that the various aspects described above relate to solution of technical problems related to providing suction via a mirror holder at a place where liquids accumulate, without regard to an angular position of the mirror holder and/or an angular position of a patient's head.

Although the various aspects of the disclosure are presented separately above, various embodiments of the disclosure integrate two, three, four or five aspects and/or features from those aspects into a single embodiment.

In some exemplary embodiments of the disclosure there is provided a disposable apparatus including: (a) a mirror holder including a floor with a raised circumferential edge having a height≥(Height of a support base+thickness of the mirror); (b) three or more deformable posts distributed around an inner side of the circumferential edge; (c) a plurality of the support bases, each of the bases adjacent to one of the posts on an inner side of the post; and (d) a suction tube with a mouth spanning a plane of a mirror positioned on the bases and a rear opening across the tube from the mouth. In some embodiments, the apparatus includes four or more deformable posts. Alternatively or additionally, in some embodiments the apparatus is constructed of a thermoplastic polymer. Alternatively or additionally, in some embodiments the raised circumferential edge has an outer diameter of about 23 to about 27 mm. Alternatively or additionally, in some embodiments the raised circumferential edge has an inner diameter of about 20.75 to about 24.75 mm. Alternatively or additionally, in some embodiments the deformable posts have a pre-deformation width of about 1.4 to about 1.5 mm. Alternatively or additionally, in some embodiments the bases have a diameter of about 1.4 to about 2 mm to about 3 mm. Alternatively or additionally, in some embodiments the deformable posts have a pre-deformation height of about 3.8 mm to about 5 mm. Alternatively or additionally, in some embodiments the bases have a height of about 1.5 mm to about 3 mm. Alternatively or additionally, in some embodiments the apparatus includes raised ribs on the floor. Alternatively or additionally, in some embodiments the apparatus includes three or more slots distributed around the circumferential edge, each of the slots providing an opening through the floor and at least a portion of a height of the raised circumferential edge. Alternatively or additionally, in some embodiments an aspect ratio of the mouth to the rear opening (cross sectional area to cross sectional area) is in the range of about 2.4:1 to about 2.8:1. Alternatively or additionally, in some embodiments the apparatus includes a mirror positioned on the support bases. Alternatively or additionally, in some embodiments the mirror includes glycol-modified polyethylene terephthalate (PETG).

In some exemplary embodiments of the disclosure there is provided a disposable apparatus including: (a) a mirror holder including a floor with a raised circumferential edge extending at least to a plane of a top surface of a mirror seated in the holder; (b) a suction tube with a mouth spanning a plane of a mirror seated in the holder; and (c) raised ribs on the floor, the ribs positioned to create air channels below the mirror from slots distributed around the circumferential edge to the mouth and/or from a gap surrounding the mirror to the mouth. In some embodiments, each of the slots provides an opening through the floor and at least a portion of a height of the raised circumferential edge. Alternatively or additionally, in some embodiments the apparatus includes a rear opening across the suction tube from the mouth. Alternatively or additionally, in some embodiments an aspect ratio of the mouth to the rear opening (cross sectional area to cross sectional area) is in the range of about 2.4:1 to about 2.8:1. Alternatively or additionally, in some embodiments the apparatus includes a bump in a center of the floor. Alternatively or additionally, in some embodiments the apparatus includes a mirror positioned on the raised ribs. Alternatively or additionally, in some embodiments the mirror includes glycol-modified polyethylene terephthalate (PETG).

In some exemplary embodiments of the disclosure there is provided a disposable apparatus including: (a) a mirror holder including a floor with raised circumferential edge; (b) a suction tube with a mouth spanning a plane of a mirror seated in the holder, the tube connected to the mirror holder; (c) an angled collar on the suction tube; and (d) an extension tube with an end cut at an angle to match the collar. In some embodiments, the apparatus includes slots distributed around the circumferential edge. Alternatively or additionally, in some embodiments each of the slots provides an opening through the floor and at least a portion of a height of the raised circumferential edge. Alternatively or additionally, in some embodiments the apparatus includes a rear opening across the suction tube from the mouth. Alternatively or additionally, in some embodiments an aspect ratio of the mouth to the rear opening (cross sectional area to cross sectional area) is in the range of about 2.4:1 to about 2.8:1. Alternatively or additionally, in some embodiments the apparatus includes raised ribs on the floor. Alternatively or additionally, in some embodiments the apparatus includes a mirror positioned on raised ribs. Alternatively or additionally, in some embodiments the mirror includes glycol-modified polyethylene terephthalate (PETG).

In some exemplary embodiments of the disclosure there is provided a disposable apparatus comprising: (a) mirror holder including a floor with a raised circumferential edge; (b) a suction tube with a mouth spanning a plane of a mirror seated in the holder, the tube tapering towards an end distal to the mirror holder; the tube connected to the holder; and (c) an extension tube with an end having an inner diameter greater than an outer diameter of the end distal to the mirror holder of the suction tube. In some embodiments, the apparatus includes an angled collar on the suction tube and an end of the extension tube cut at an angle to match the collar. Alternatively or additionally, in some embodiments the apparatus includes slots distributed around the circumferential edge. Alternatively or additionally, in some embodiments each of the slots provides an opening through the floor and at least a portion of a height of the raised circumferential edge. Alternatively or additionally, in some embodiments the apparatus includes a rear opening across the suction tube from the mouth. Alternatively or additionally, in some embodiments an aspect ratio of the mouth to the rear opening (cross sectional area to cross sectional area) is in the range of about 2.4:1 to about 2.8:1. Alternatively or additionally, in some embodiments the apparatus includes raised ribs on the floor. Alternatively or additionally, in some embodiments an outer diameter of the suction tube tapers towards its distal end.

In some exemplary embodiments of the disclosure there is provided a manufacturing method including: positioning a mirror holder including a floor and raised circumferential edge with 3 or more deformable posts distributed around an inner side of the circumferential and a support base adjacent to each of the posts on its inner side in a holder; placing a mirror on the support bases; and lowering a heated piston with sufficient force to deform the posts so that they retain the mirror on the bases. In some embodiments, the method includes heating the piston to a deformation temperature of a thermoplastic polymer from which the deformable posts are constructed. Alternatively or additionally, in some embodiments the sufficient force is at least about 45 psi (310264.07819 newton/square meters). Alternatively or additionally, in some embodiments the sufficient force is applied for at least 1.5 seconds. Alternatively or additionally, in some embodiments the mirror holder includes a thermoplastic polymer selected from the group consisting of Polyethylene (PE) and High Density Polyethylene (HDPE). Alternatively or additionally, in some embodiments the deformable posts comprise a thermoplastic polymer selected from the group consisting of Polyethylene (PE) and High Density Polyethylene (HDPE). Alternatively or additionally, in some embodiments the mirror includes at least one material selected from the group consisting of glycol-modified polyethylene terephthalate (PETG), acrylic plastic and polycarbonate.

For purposes of this specification and the accompanying claims, the term “disposable” indicates an item that is rendered unusable by autoclaving at routine sterilization conditions for dental instruments.

Unless otherwise defined, all technical and scientific terms used herein have the same meaning as commonly understood by one of ordinary skill in the art to which this disclosure belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

As used herein, the terms “comprising” and “including” or grammatical variants thereof are to be taken as specifying inclusion of the stated features, integers, actions or components without precluding the addition of one or more additional features, integers, actions, components or groups thereof. This term is broader than, and includes the terms “consisting of” and “consisting essentially of” as defined by the Manual of Patent Examination Procedure of the United States Patent and Trademark Office. Thus, any recitation that an embodiment “includes” or “comprises” a feature is a specific statement that sub embodiments “consist essentially of” and/or “consist of” the recited feature.

The phrase “consisting essentially of” or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The phrase “adapted to” as used in this specification and the accompanying claims imposes additional structural limitations on a previously recited component.

The term “method” refers to manners, means, techniques and procedures for accomplishing a given task including, but not limited to, those manners, means, techniques and procedures either known to, or readily developed from known manners, means, techniques and procedures by practitioners of architecture and/or computer science.

BRIEF DESCRIPTION OF THE DRAWINGS

In order to understand the disclosure and to see how it may be carried out in practice, embodiments will now be described, by way of non-limiting example only, with reference to the accompanying figures. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DETAILED DESCRIPTION OF EMBODIMENTS

Embodiments of the disclosure relate to a disposable dental mirror holder apparatus, the holder with a mirror installed and a method of affixing the mirror to the holder.

Specifically, some embodiments of the disclosure can be used to contribute to a reduction in the need to remove a dental mirror from a patient’s mouth during a dental procedure for cleaning.

The principles and operation of an apparatus and/or methodic according to exemplary embodiments of the disclosure may be better understood with reference to the drawings and accompanying descriptions.

Before explaining at least one embodiment of the disclosure in detail, it is to be understood that the disclosure is not limited in its application to the details set forth in the following description or exemplified by the Examples. The disclosure is capable of other embodiments or of being practiced or carried out in various ways. Also, it is to be understood that the phraseology and terminology employed herein is for the purpose of description and should not be regarded as limiting.

Exemplary Apparatus

Figures 1A, 1B:
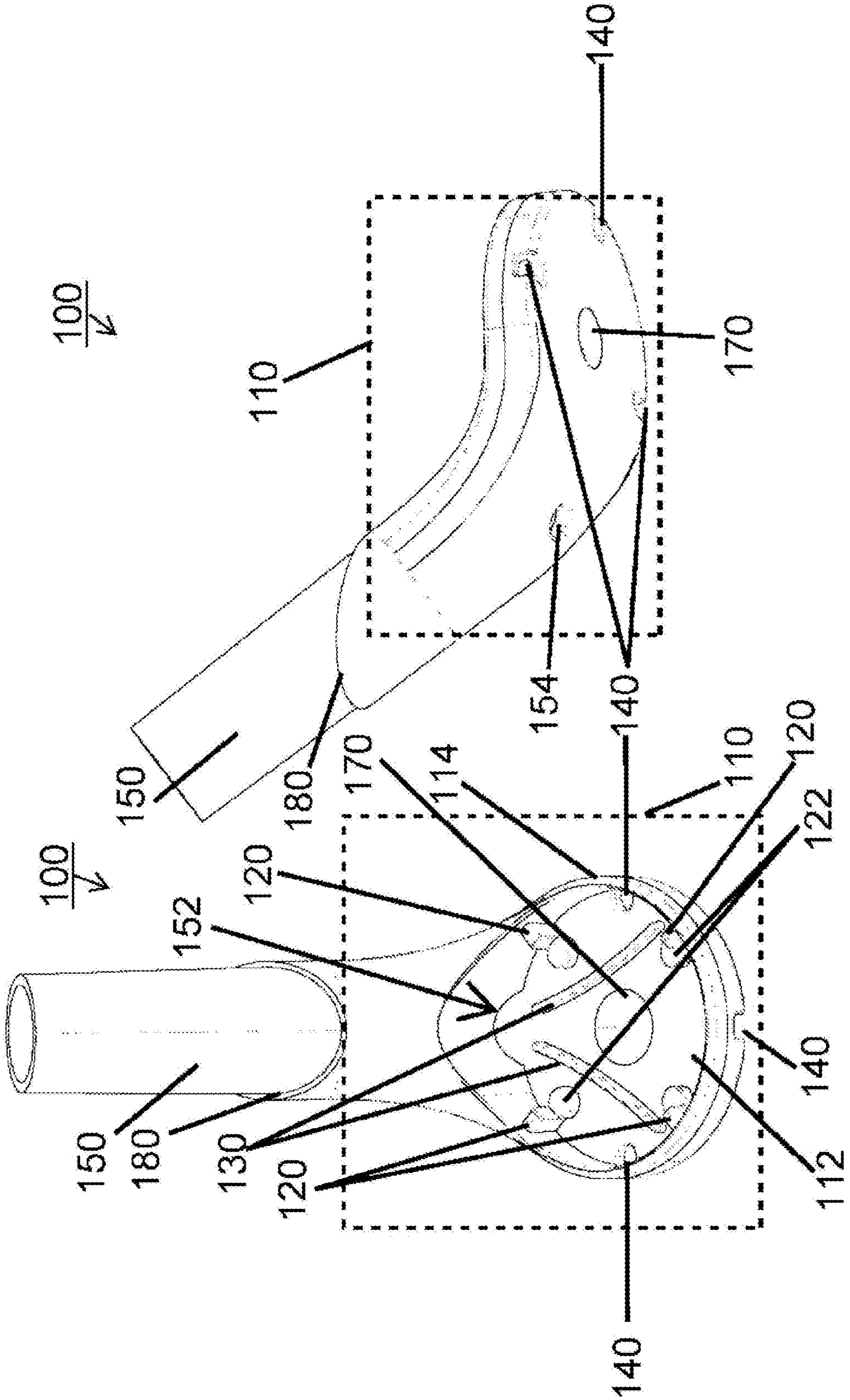
FIG. 1*a* is a front perspective view from above of an apparatus according to some exemplary embodiments of the disclosure with mirror removed.
FIG. 1*b* is a rear perspective view from below of an apparatus according to some exemplary embodiments of the invention.

FIG. 1*a* is a front perspective view from above of a disposable dental mirror holder apparatus, indicated generally as 100, according to some exemplary embodiments of the disclosure with mirror removed.

FIG. 1*b* is a rear perspective view from below of an apparatus as in FIG. 1*a*.

Figure 1D:
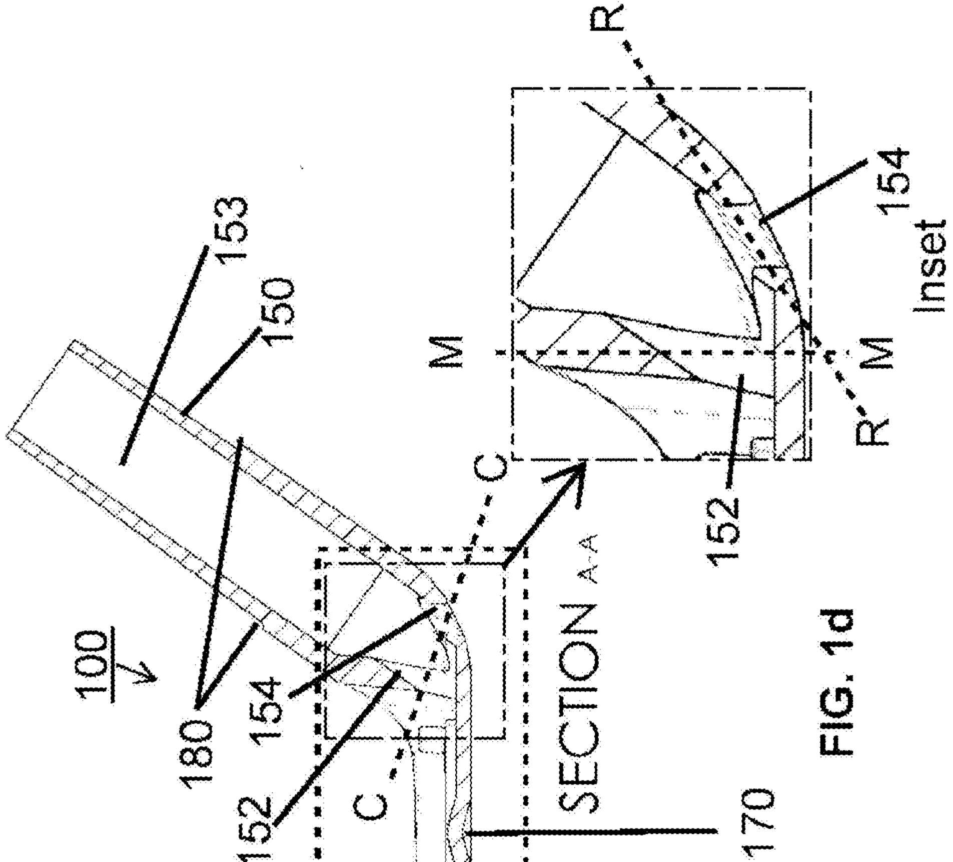
FIG. 1*d* is a cross sectional view of the apparatus of FIG. 1*c* through section line A-A with a portion enlarged in an inset.
Figure 1C:
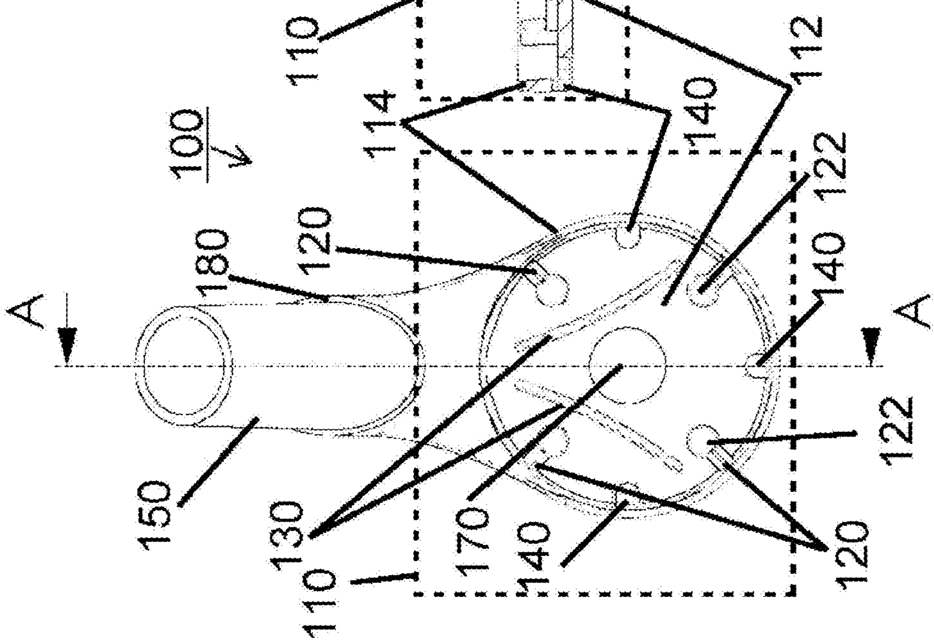
FIG. 1*c* is a top view of an apparatus according to some exemplary embodiments of the disclosure with mirror removed with section line A-A.

FIG. 1*c* is a top view of an apparatus as in FIG. 1*a* with section line A-A.

FIG. 1*d* is a cross sectional view of the apparatus of FIG. 1*c* through section line A-A with a portion shown enlarged in an inset.

Figure 2A:
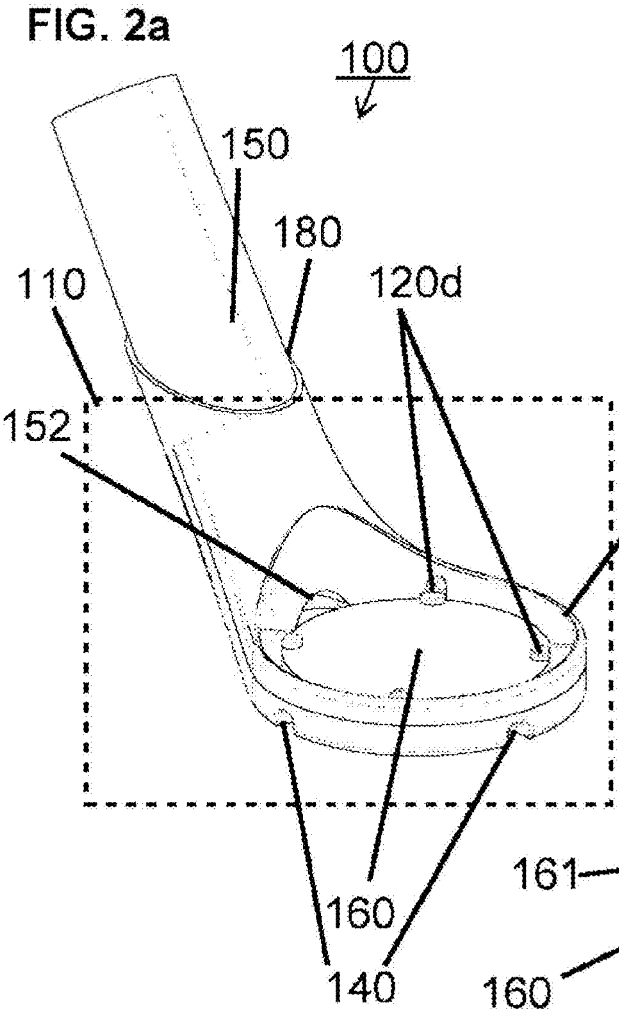
FIG. 2*a* is a front perspective view from above of an apparatus as in FIG. 1*a* with mirror installed.

FIG. 2*a* is a front perspective view from above of an apparatus as in FIG. 1*a* with mirror installed.

Figure 2B:
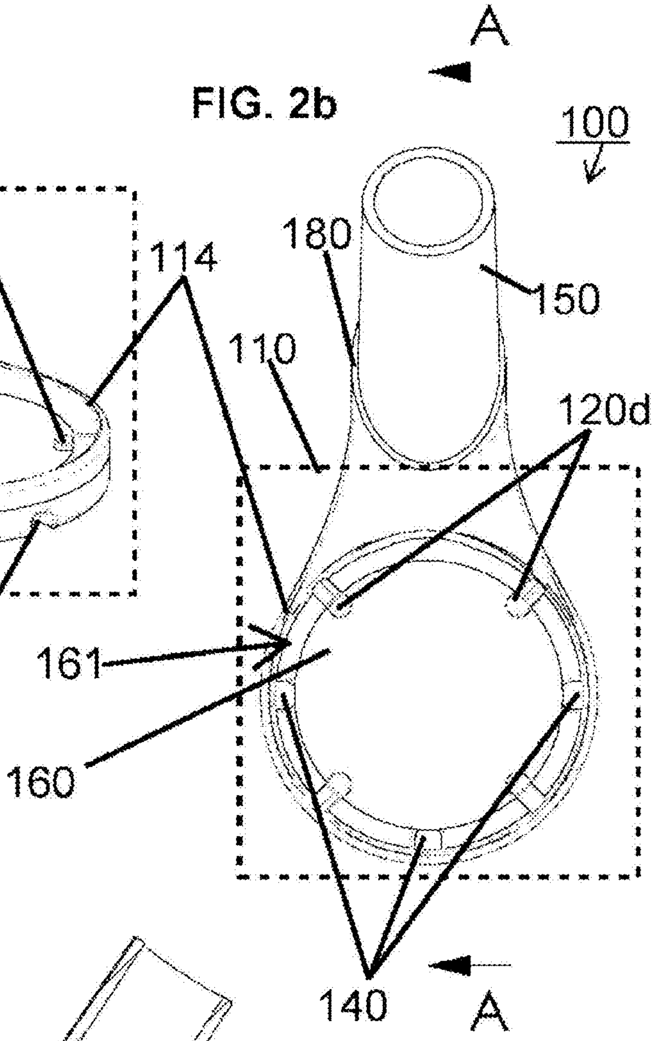
FIG. 2*b* is a top view of an apparatus according to some exemplary embodiments of the disclosure with mirror installed with section line A-A.

FIG. 2*b* is a top view of an apparatus as in FIG. 2*a* with section line A-A.

Figure 2C:
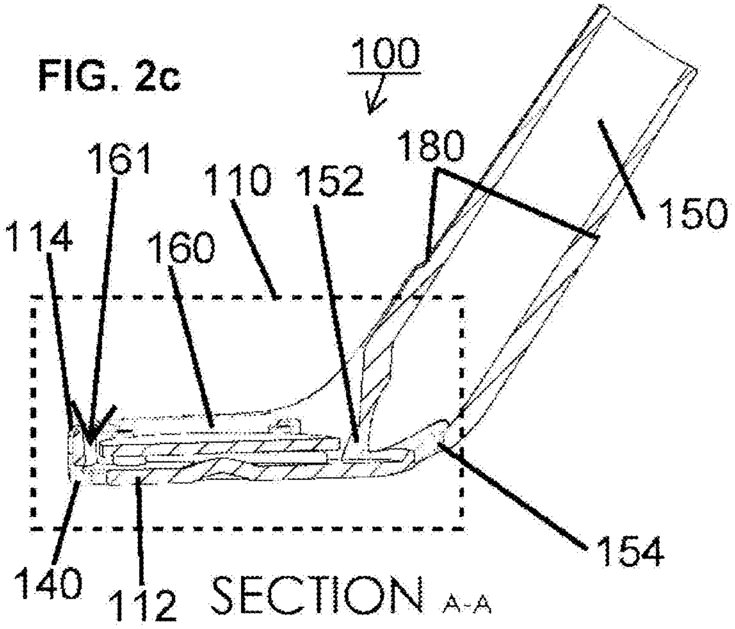
FIG. 2*c* is a cross sectional view of the apparatus of FIG. 2*b* through section line A-A.

FIG. 2*c* is a cross sectional view of the apparatus of FIG. 2*b* through section line A-A.

Depicted exemplary apparatus 100 includes a mirror holder 110 including a floor 112 with a raised circumferential edge 114. In some embodiments, edge 114 has a height≥ (Height of a support base 122+thickness of a mirror 160). In the depicted embodiment, apparatus 100 has three or more deformable posts 120 (four are depicted; in other embodiments larger numbers are provided) distributed around an inner side of circumferential edge 114. In the depicted embodiment, apparatus 100 includes a plurality of support bases 122. Each of bases 122 is adjacent to one of posts 120 on an inner side of the post. In use, posts 120 are deformed so that they engage and retain a mirror 160 (See deformed posts 120*d* in FIG. 2*a* and FIG. 2*b*).

Depicted exemplary apparatus 100 includes a suction tube 150 with a mouth 152 spanning a plane of a mirror 160 positioned on bases 122 and a rear opening 154 (visible in FIG. 1*b*) across tube 150 from mouth 152. For purposes of this specification and the accompanying claims, the term "across said tube" or "across the tube" indicates that it is possible to look through mouth 152 and see out of rear opening 154, or the opposite as indicated by line C-C in FIG. 1*d*.

In some embodiments, apparatus 100 is constructed of a thermoplastic polymer. Thermoplastic polymers suitable for use in the context of exemplary embodiments of the disclosure include, but are not limited to, Polyethylene (PE) and High Density Polyethylene (HDPE). In some exemplary embodiments of the invention, the apparatus is formed by injection molding. In some exemplary embodiments of the invention, HIVAL® 521054 High Density Polyethylene (by Nexeo®) is used.

For common commercial grades of medium- and high-density polyethylene the melting point is typically in the range 120° C. to 130° C. (248° F. to 266° F.). The melting point for average commercial low-density polyethylene is typically 105° C. to 115° C. (221° F. to 239° F.)

In some exemplary embodiments of the invention, raised circumferential edge 114 has an outer diameter of about 23 to about 27 mm. Alternatively or additionally, in some embodiments raised circumferential edge 114 has an inner diameter of about 20.75 to about 24.75 mm. Alternatively or additionally, in some embodiments deformable posts 120 have a pre-deformation width of about 1.4 to about 1.5 mm. Alternatively or additionally, in some embodiments bases 122 have a diameter of about 1.4 to about 2 mm to about 3 mm. Alternatively or additionally, in some embodiments posts 120 have a pre-deformation height of about 3.8 mm to about 5 mm, optionally about 4.25 mm. In use, a 4.25 mm post is deformed to about 3.75 to about 3.9 mm, in some cases about 3.81 mm. Alternatively or additionally, in some embodiments bases 122 have a height of about 1.5 mm to about 3 mm, in some embodiments about 2.2 mm.

In the depicted embodiment, apparatus 100 includes raised ribs 130 on floor 112. In some embodiments, ribs 130 support mirror 160. In some embodiments, this support contributes to a reduced tendency towards deformation of mirror 160 during use.

In the depicted embodiment, apparatus 100 includes three or more slots 140 distributed around circumferential edge 114, each of slots 140 providing an opening through floor 112 and at least a portion of a height of raised circumferential edge 114.

In some embodiments ribs 130 (either alone or in cooperation with raised edge 114) contribute to the creation air channels leading to mouth 152 below mirror 160.

For example, referring to FIG. 1*a* and FIG. 1*c*, air entering via slot 140 on the left is conducted through an air channel formed by edge 114 and left rib 130 (and mirror 160) to mouth 152, air entering via medial slot 140 is conducted through an air channel formed by ribs 130 (and mirror 160) to mouth 152, and air entering via slot 140 on the right is conducted through an air channel formed by edge 114 and right rib 130 (and mirror 160) to mouth 152. In some embodiments, segregation of the airflow into separate channels contributes to a reduction in turbulence and/or contributes to an increase in suction efficiency. These air channels also divide air entering via gap 161 (see FIG. 2*b* and FIG. 2*c*) and contribute to a reduction in its turbulence with similar results.

In some exemplary embodiments of the invention, an aspect ratio of mouth 152 to rear opening 154 (cross sectional area to cross sectional area) is in the range of about 2.4:1 to about 2.8:1, in some embodiments about 2.6:1. For purposes of this specification and the accompanying claims, every reference to an "an aspect ratio of mouth 152 to rear opening 154 (cross sectional area to cross sectional area)" refers to measurements of mouth 152 made in a cross-sectional plane of the mouth containing line M-M as depicted in the inset of FIG. 1*d* and refers to measurements of rear opening 154 made in a cross-sectional plane of the opening containing line R-R as depicted in the inset of FIG. 1*d*.

In some embodiments, apparatus 100 includes a mirror 160 positioned on support bases 122 (See FIG. 2*a* and compare to FIG. 1*a*). In some exemplary embodiments of the invention, mirror 160 includes glycol-modified polyethylene terephthalate (PETG). In some embodiments, PETG contributes to a reduced tendency towards fogging and/or contributes to disposability.

Additional Exemplary Apparatus

Referring still to FIG. 1*a*, FIG. 1*b*, FIG. 1*c*, FIG. 1*d*. FIG. 2*a*, FIG. 2*b*, and FIG. 2*c*:

Depicted exemplary apparatus 100 includes a mirror holder 110 including a floor 112 with a raised circumferential edge 114 extending at least to a plane of a top surface of a mirror 160 seated in holder 110.

In the depicted embodiment, apparatus 100 includes a suction tube 150 with a mouth 152 spanning a plane of a mirror 160 seated in holder 110 and raised ribs 130 on floor 112, ribs 130 positioned to create air channels below the mirror 160 from slots 140 distributed around circumferential edge 114 to mouth 152. Alternatively or additionally, in the depicted embodiment, air channels below mirror 160 facilitate a flow of air from gap 161 surrounding mirror 160 to mouth 152.

The air channels and their function(s) are described hereinabove.

In some embodiments of apparatus 100, each of slots 140 provides an opening through floor 112 and at least a portion of a height of raised circumferential edge 114. Alternatively or additionally, in some embodiments of apparatus 100, there is a rear opening 154 across suction tube 150 from mouth 152. In some exemplary embodiments of the invention, an aspect ratio of mouth 152 to rear opening 154 (cross sectional area to cross sectional area) is in the range of about 2.4:1 to about 2.8:1.

In some exemplary embodiments of the invention, Apparatus 100 includes a bump 170 in a center of floor 112. Alternatively or additionally, in some embodiments apparatus 100 includes a mirror 160 positioned on raised ribs 130. In some embodiments, mirror 160 comprises glycol-modified polyethylene terephthalate (PETG) which has properties as described hereinabove. Alternatively or additionally, in some embodiments mirror 160 comprises acrylic plastic and/or polycarbonate.

Another Additional Exemplary Apparatus

Figure 3:
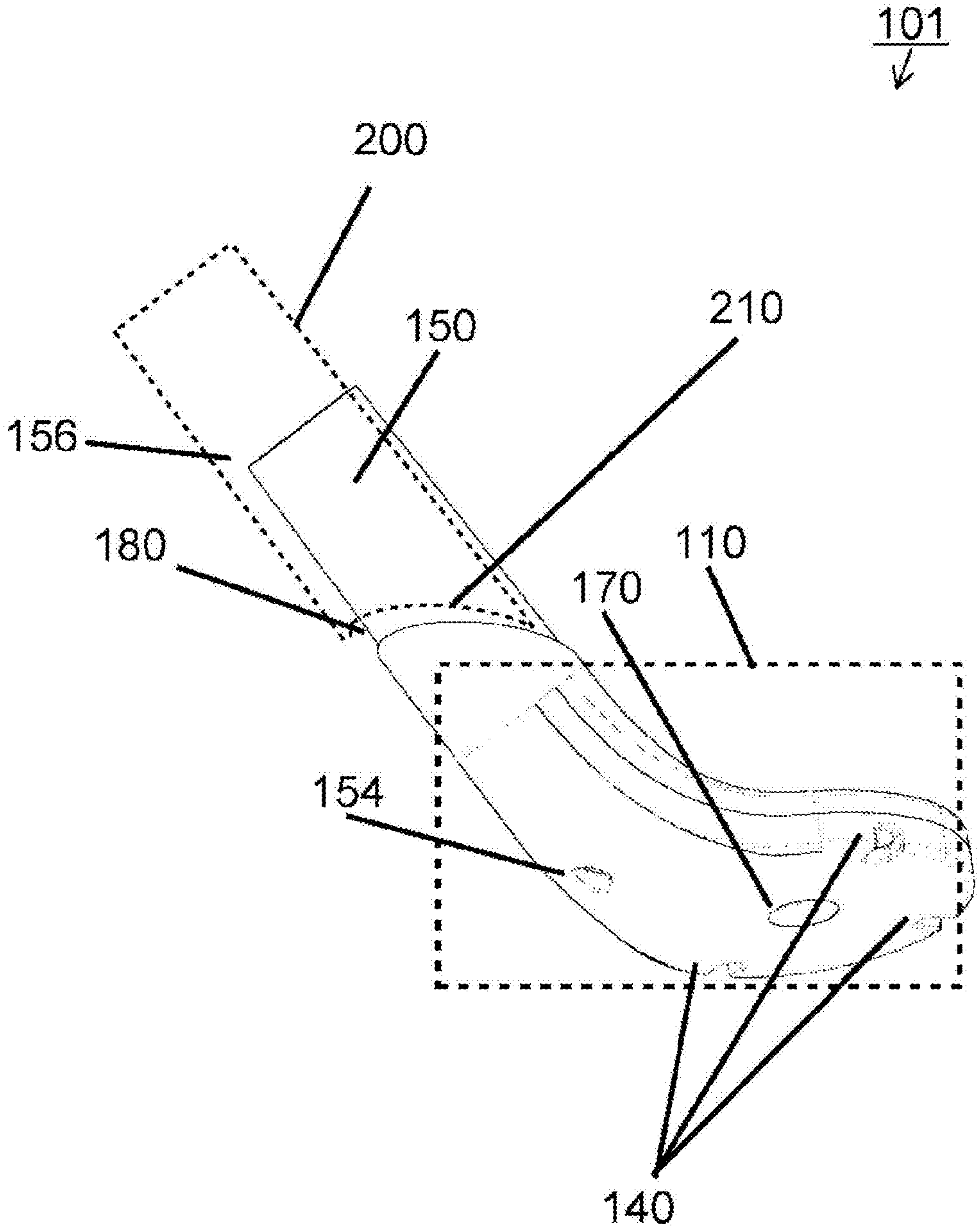
FIG. 3 is a is a rear perspective view from below of an apparatus according to some exemplary embodiments of the invention.

FIG. 3 is a rear perspective view from below of an apparatus, indicated generally as 101 according to some exemplary embodiments of the invention.

Referring now to FIG. 3 as well as FIG. 1*a*, FIG. 1*b*, FIG. 1*c*, FIG. 1*d*. FIG. 2*a*, FIG. 2*b*, and FIG. 2*c:*

In some exemplary embodiments of the invention, disposable apparatus 101 includes a mirror holder 110 including a floor 112 with raised circumferential edge 114 and a suction tube 150 with a mouth 152 spanning a plane of a mirror 160 seated in the holder, tube 150 connected to mirror holder 110 (or integrally formed therewith).

Apparatus 101 includes an angled collar 180 on suction tube 150 and an extension tube 200 with an end 210 cut at an angle to match collar 180. In some exemplary embodiments of the invention, apparatus 101 includes slots 140 distributed around circumferential edge 114. In some embodiments, each of slots 140 provides an opening through floor 112 and at least a portion of a height of raised circumferential edge 114. Alternatively or additionally, in some embodiments apparatus 101 includes a rear opening 154 across suction tube 150 from mouth 152. In some exemplary embodiments of the invention, an aspect ratio of mouth 152 to rear opening 154 (cross sectional area to cross sectional area) is in the range of about 2.4:1 to about 2.8:1, in some embodiments about 2.6:1. Alternatively or additionally, in some embodiments apparatus 101 includes raised ribs 130 on floor 112. In some exemplary embodiments of the invention, apparatus 101 includes a mirror 160 positioned on raised ribs 130. In some embodiments, the mirror comprises glycol-modified polyethylene terephthalate (PETG) which has properties as described hereinabove. Alternatively or additionally, in some embodiments mirror 160 comprises acrylic plastic and/or polycarbonate.

Another Further Additional Exemplary Apparatus

Referring still to FIG. 3 as well as FIG. 1*a*, FIG. 1*b*, FIG. 1*c*, FIG. 1*d*. FIG. 2*a*, FIG. 2*b*, and FIG. 2*c:*

In the depicted embodiment, apparatus 101 includes a mirror holder 110 including a floor 112 with a raised circumferential edge 114 and a suction tube 150 with a mouth 152 spanning a plane of a mirror 160 seated in holder 110. In the depicted embodiment, an outer diameter of tube 150 tapers towards an end 156 distal to the mirror holder 110. In the depicted embodiment, tube 150 is connected to mirror holder 110 (or integrally formed therewith).

Depicted exemplary apparatus 101 also includes an extension tube 200 with an end 210 having an inner diameter greater than an outer diameter of end 156 distal to mirror holder 110 of suction tube 150.

In the depicted embodiment, apparatus 101 includes an angled collar 180 on suction tube 150 and an end 210 of extension tube 200 cut at an angle to match collar 180. Extension tube 200 and end 210 are drawn with dashed lines to more clearly depict the spatial relationship between extension tube 200 and suction tube 150. Alternatively or additionally, in some embodiments apparatus 101 includes slots 140 distributed around circumferential edge 114. In some embodiments, each of slots 140 provides an opening through floor 112 and at least a portion of a height of raised circumferential edge 114. Alternatively or additionally, in some embodiments apparatus 101 includes a rear opening 154 across suction tube 150 from mouth 152. In some exemplary embodiments of the invention, an aspect ratio of mouth 152 to rear opening 154 (cross sectional area to cross sectional area) is in the range of about 2.4:1 to about 2.8:1, in some embodiments about 2.6:1. Alternatively or additionally, in some embodiments apparatus 101 includes raised ribs 130 on said floor. In some exemplary embodiments of the invention, an outer diameter of suction tube 150 tapers towards its distal end 156. As a result extension tube 200 engages suction tube 150 with increasing snugness as it progresses towards collar 180. Contact of distal end 210 of extension tube 200 with collar 180 on suction tube 150 contributes to a reduction in the ability of extension tube 200 to progress further along suction tube 150. Alternatively or additionally, contact of distal end 210 of extension tube 200 with collar 180 on suction tube 150 contributes to a reduction in the possibility of relative rotational motion between extension tube 200 and suction tube 150.

Exemplary Method

Figure 4:
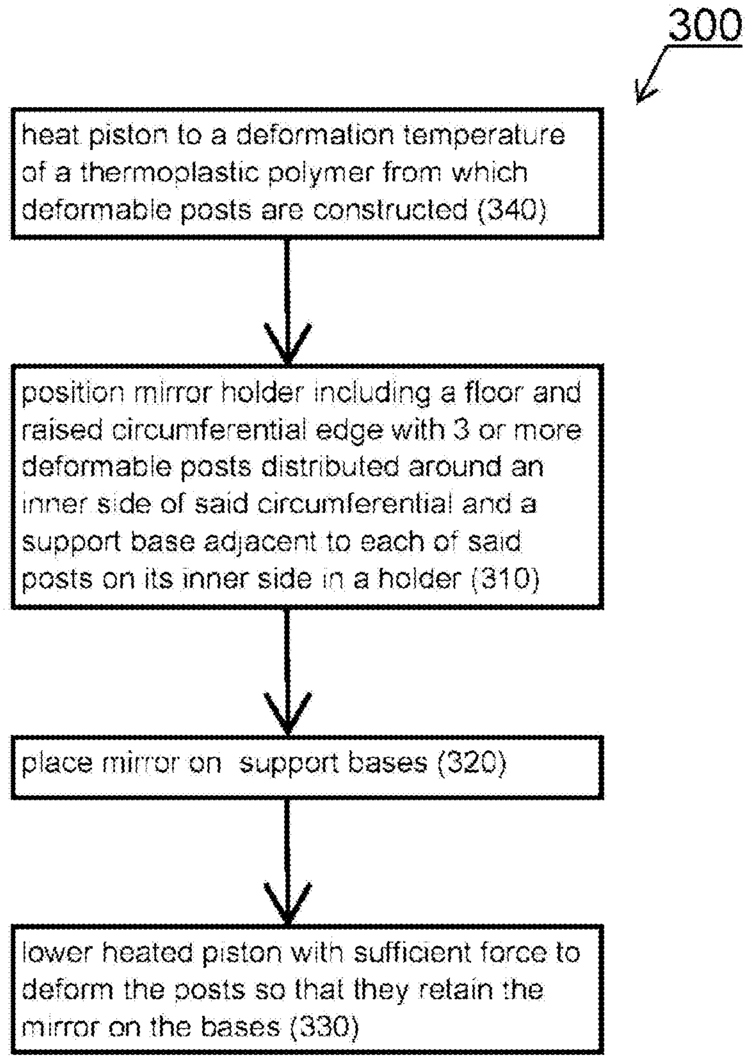
FIG. 4 is a simplified flow diagram of a method according to some exemplary embodiments of the invention.

FIG. 4 is a simplified flow diagram of a method of manufacture, indicated generally as 300, according to some exemplary embodiments of the invention.

Depicted exemplary method 300 includes positioning 310 a mirror holder including a floor and raised circumferential edge with three or more deformable posts distributed around an inner side of said circumferential and a support base adjacent to each of said posts on its inner side in a holder, placing 320 a mirror on the support bases and lowering 330 a heated piston with sufficient force to deform the posts so that they retain the mirror on the bases.

In some embodiments, method 300 includes heating 340 the piston to a deformation temperature of a thermoplastic polymer from which the deformable posts are constructed. (Relevant temperatures for common thermoplastic polymers suitable for use in the context of embodiments of the disclosure are provided hereinabove.) In some embodiments, the sufficient force is at least about 45 psi (310264.07819 newton/square meters).

Alternatively or additionally, in some embodiments the sufficient force is applied for 1.5 seconds, 2 seconds, 3 seconds, 4 seconds, 5 seconds, 6 seconds, 7 seconds, 8 seconds, 9 seconds or intermediate or greater amounts of time. According to various exemplary embodiments of the disclosure the mirror holder comprises a thermoplastic polymer selected from the group consisting of Polyethylene (PE) and High Density Polyethylene (HDPE). Alternatively or additionally, according to various exemplary embodiments of the disclosure the deformable posts comprise a thermoplastic polymer selected from the group consisting of Polyethylene (PE) and High Density Polyethylene (HDPE). In some embodiments, the mirror comprises glycol-modified polyethylene terephthalate (PETG) Which has properties as described hereinabove. Alternatively or additionally, in some embodiments mirror 160 comprises acrylic plastic and/or polycarbonate.

Exemplary Theoretical Considerations

In use, apparatus 100 or 101 as described above is connected to an external suction source which draws air in via slots 140, rear opening 154, mouth 152 and gap 161. This air is drawn through an inner lumen 153 of suction tube 150 and out of the apparatus.

When apparatus 100 or 101 is placed in a patient's mouth: a first subset of slots 140, rear opening 154, mouth 152 and a portion of gap 161 may contact an accumulation of liquid in a patient's mouth at a given moment. At that moment, a complementary subset of slots 140, rear opening 154, mouth 152 and a portion of gap 161 that is not in contact with the accumulation of liquid continues to draw in air which finds its way to inner lumen 153 of suction tube 150 where it is drawn out of the apparatus by the external suction source.

In some exemplary embodiments of the invention, this air drawn in through the complementary subset of slots 140, rear opening 154, mouth 152 and a portion of gap 161 that is not in contact with the accumulation of liquid create a Venturi effect which contribute to a tendency of accumulated liquid from the patient's mouth drawn in via the first subset of slots 140, rear opening 154, mouth 152 and a portion of gap 161 to move towards lumen 153 of suction tube 150.

It is expected that during the life of this patent many thermoplastic polymers will be developed and the scope of the disclosure includes all such new technologies a priori.

As used herein the term "about" refers to ±10%.

Although the disclosure has been described in conjunction with specific embodiments thereof, it is evident that many alternatives, modifications and variations will be apparent to those skilled in the art. Accordingly, the disclosure embraces all such alternatives, modifications and variations that fall within the scope of the appended claims.

Specifically, a variety of numerical indicators have been utilized. It should be understood that these numerical indicators could vary even further based upon a variety of engineering principles, materials, intended use and designs incorporated into the various embodiments of the invention. Additionally, components and/or actions ascribed to exemplary embodiments of the disclosure and depicted as a single unit may be divided into subunits. Conversely, components and/or actions ascribed to exemplary embodiments of the disclosure and depicted as sub-units/individual actions may be combined into a single unit/action with the described/depicted function.

Alternatively, or additionally, features used to describe a method can be used to characterize an apparatus and features used to describe an apparatus can be used to characterize a method.

It should be further understood that the individual features described hereinabove can be combined in all possible combinations and sub-combinations to produce additional embodiments of the invention. The examples given above are exemplary in nature and do not limit the scope of the disclosure which is defined solely by the following claims.

Each recitation of an embodiment of the disclosure that includes a specific feature, part, component, module or process is an explicit statement that additional embodiments of the disclosure not including the recited feature, part, component, module or process exist.

Alternatively or additionally, various exemplary embodiments of the disclosure exclude any specific feature, part, component, module, process or element which is not specifically disclosed herein.

Specifically, the disclosure has been described in the context of dental procedures but might also be used in other medical or surgical contexts.

All publications, references, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include", and "have" and their conjugates as used herein mean "including but not necessarily limited to".

What is claimed is:

1. A disposable apparatus comprising:

(a) a mirror holder including a floor with a raised circumferential edge having a height≥(Height of a support base+thickness of the mirror);

(b) three or more deformable posts distributed around an inner side of said circumferential edge;

(c) a plurality of said support bases, each of said bases adjacent to one of said posts on an inner side of the post; and (d) a suction tube with a mouth spanning a plane of a mirror positioned on said bases and a rear opening across said tube from said mouth.

2. An apparatus according to claim 1, comprising four or more deformable posts.

3. An apparatus according to claim 1, constructed of a thermoplastic polymer.

4. An apparatus according to claim 1, wherein said raised circumferential edge has an outer diameter of about 23 to about 27 mm.

5. An apparatus according to claim 1, wherein said raised circumferential edge has an inner diameter of about 20.75 to about 24.75 mm.

6. An apparatus according to claim 1, wherein said deformable posts have a pre-deformation width of about 1.4 to about 1.5 mm.

7. An apparatus according to claim 1, wherein said bases have a diameter of 1.4 to 3 mm.

8. An apparatus according to claim 1, wherein said deformable posts have a pre-deformation height of about 3.8 mm to about 5 mm.

9. An apparatus according to claim 1, wherein said bases have a height of about 1.5 mm to about 3 mm.

10. An apparatus according to claim 1, comprising raised ribs on said floor.

11. An apparatus according to claim 1, comprising three or more slots distributed around said circumferential edge, each of said slots providing an opening through said floor and at least a portion of a height of said raised circumferential edge.

12. A disposable apparatus according to claim 1 comprising:

a mirror holder including a floor with a raised circumferential edge extending at least to a plane of a top surface of a mirror seated in the holder;

a suction tube with a mouth spanning a plane of a mirror seated in the holder; and raised ribs on said floor, the ribs positioned to create air channels below the mirror from slots distributed around said circumferential edge to said mouth.

13. An apparatus according to claim 12, wherein each of said slots provides an opening through said floor and at least a portion of a height of said raised circumferential edge.

14. An apparatus according to claim 12, comprising a rear opening across said suction tube from said mouth.

15. An apparatus according to claim 14, wherein an aspect ratio of said mouth to said rear opening (cross sectional area to cross sectional area) is in the range of about 2.4:1 to about 2.8:1.

16. An apparatus according to claim 12, comprising a bump in a center of the floor.

* * * * *